US008211102B2

(12) United States Patent
Paul et al.

(10) Patent No.: US 8,211,102 B2
(45) Date of Patent: *Jul. 3, 2012

(54) CONTACT SENSING FLEXIBLE CONDUCTIVE POLYMER ELECTRODE

(75) Inventors: Saurav Paul, Minnetonka, MN (US); Chou Thao, Brooklyn Park, MN (US); Troy T. Tegg, Elk River, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1169 days.

This patent is subject to a terminal disclaimer.

(21) Appl. No.: 11/963,321

(22) Filed: Dec. 21, 2007

(65) Prior Publication Data

US 2009/0158852 A1   Jun. 25, 2009

(51) Int. Cl.
*A61B 18/14* (2006.01)
(52) U.S. Cl. ........................................ 606/41
(58) Field of Classification Search ............... 606/27, 606/32–35, 41, 42, 48–50
See application file for complete search history.

(56) References Cited

U.S. PATENT DOCUMENTS

| | | |
|---|---|---|
| 4,911,174 A | 3/1990 | Pederson et al. |
| 4,945,912 A | 8/1990 | Langberg |
| 5,122,137 A | 6/1992 | Lennox |
| 5,246,438 A | 9/1993 | Langberg |
| 5,341,807 A | 8/1994 | Nardella |
| 5,372,603 A | 12/1994 | Acker et al. |
| 5,382,247 A | 1/1995 | Cimino et al. |
| 5,433,708 A | 7/1995 | Nichols |
| 5,447,529 A | 9/1995 | Marchlinski |
| 5,447,539 A | 9/1995 | Kelly et al. |
| 5,472,441 A | 12/1995 | Edwards et al. |
| 5,542,928 A | 8/1996 | Evans |
| 5,545,161 A | 8/1996 | Imran |
| 5,697,925 A | 12/1997 | Taylor |
| 5,836,990 A | 11/1998 | Li |

(Continued)

FOREIGN PATENT DOCUMENTS

WO    WO2005039835    5/2005

OTHER PUBLICATIONS

International Search Report and Written Opinion for PCT/US08/86984 filed Dec. 16, 2008, dated Feb. 10, 2009.

(Continued)

*Primary Examiner* — Linda Dvorak
*Assistant Examiner* — Khadijeh Vahdat
(74) *Attorney, Agent, or Firm* — Wiley Rein LLP (57) ABSTRACT

A contact sensing catheter system includes a catheter shaft having a distal end; a flexible conductive polymer electrode located at the distal end of the shaft; and an electro-mechanical contact sensor positioned at least partially within the electrode. The sensor outputs an electrical signal in response to a mechanical force acting thereon. The sensor may be a piezoelectric sensor, a strain gauge, a fiber optic sensor, or another suitable electro-mechanical contact sensor. The electrical signal output by the sensor typically varies in response to variations in the mechanical force acting on the sensor. An output device may receive the signal output by the contact sensor and present to a user of the system an indicator of contact between the electrode and a tissue by assessing, for example, the amplitude or periodicity of the signal.

23 Claims, 7 Drawing Sheets

U.S. PATENT DOCUMENTS

| | | | |
|---|---|---|---|
| 5,868,737 A | 2/1999 | Taylor et al. | |
| 6,013,074 A | 1/2000 | Taylor | |
| 6,039,731 A | 3/2000 | Taylor et al. | |
| 6,066,139 A | 5/2000 | Ryan et al. | |
| 6,113,592 A | 9/2000 | Taylor | |
| 6,113,593 A | 9/2000 | Tu et al. | |
| 6,171,304 B1 | 1/2001 | Netherly et al. | |
| 6,210,406 B1 | 4/2001 | Webster | |
| 6,217,573 B1 | 4/2001 | Webster | |
| 6,217,574 B1 | 4/2001 | Webster | |
| 6,246,898 B1 | 6/2001 | Vesely et al. | |
| 6,264,653 B1 | 7/2001 | Falwell | |
| 6,291,568 B1 | 9/2001 | Lussey | |
| 6,304,776 B1 | 10/2001 | Muntermann | |
| 6,322,558 B1 | 11/2001 | Taylor et al. | |
| 6,325,799 B1 | 12/2001 | Goble | |
| 6,391,024 B1 | 5/2002 | Sun et al. | |
| 6,423,057 B1 | 7/2002 | He et al. | |
| 6,495,069 B1 | 12/2002 | Lussey et al. | |
| 6,558,382 B2 * | 5/2003 | Jahns et al. | 606/41 |
| 6,616,657 B2 | 9/2003 | Simpson et al. | |
| 6,638,222 B2 | 10/2003 | Chandrasekaran et al. | |
| 6,646,540 B1 | 11/2003 | Lussey | |
| 6,696,844 B2 | 2/2004 | Wong et al. | |
| 6,730,082 B2 | 5/2004 | Messing et al. | |
| 6,845,264 B1 | 1/2005 | Skladnev et al. | |
| 6,882,885 B2 | 4/2005 | Levy, Jr. et al. | |
| 6,936,047 B2 | 8/2005 | Nasab et al. | |
| 6,974,457 B2 | 12/2005 | Gibson | |
| 6,999,821 B2 | 2/2006 | Jenney et al. | |
| 7,311,704 B2 | 12/2007 | Paul | |
| 7,326,204 B2 | 2/2008 | Paul et al. | |
| 7,326,205 B2 | 2/2008 | Paul et al. | |
| 7,326,206 B2 | 2/2008 | Paul et al. | |
| 2002/0026127 A1 * | 2/2002 | Balbierz et al. | 600/567 |
| 2002/0123749 A1 | 9/2002 | Jain | |
| 2004/0049255 A1 | 3/2004 | Jain et al. | |
| 2004/0158238 A1 * | 8/2004 | Lalonde et al. | 606/21 |
| 2007/0060847 A1 | 3/2007 | Leo et al. | |
| 2007/0100332 A1 * | 5/2007 | Paul et al. | 606/41 |
| 2008/0161789 A1 * | 7/2008 | Thao et al. | 606/34 |
| 2008/0161889 A1 * | 7/2008 | Paul et al. | 607/102 |

OTHER PUBLICATIONS

PCT International Search Report and Written Opinion of the International Searching Authority for PCT/US06/42119 dated Sep. 13, 2007.

* cited by examiner

CONTACT SENSING FLEXIBLE CONDUCTIVE POLYMER ELECTRODE

CROSS-REFERENCE TO RELATED APPLICATIONS

This application is related to U.S. application Ser. No. 11/963,430, filed Dec. 21, 2007, which is hereby incorporated by reference in its entirety as though fully set forth herein.

BACKGROUND OF THE INVENTION a. Field of the Invention

The present invention pertains generally to an electrophysiological device and method for providing energy to biological tissue and, more particularly, to an ablation apparatus with improved contact sensing capabilities.

b. Background Art

Various devices, such as electrode sensors, thermal sensors, ablation electrodes, and the like, may be implanted in catheters inserted into a patient's body (e.g., the patient's heart) for use in a wide variety of medical procedures, including, without limitation, electrophysiological mapping and tissue ablation. It is often desirable to determine the degree of contact between the device being used and the tissue the device is being used on. As used herein, the term "degree of contact" refers not only to the area of contact between the device and tissue, but also to the force being exerted by the device on the tissue (or vice versa).

By way of illustration, sensor output is only meaningful for mapping procedures when the sensors are in sufficient contact with the tissue being mapped. So-called "false signals" received when the sensor is not in good or sufficient contact with the tissue may result in inaccurate mapping of the tissue (e.g., the interior of a patient's heart).

By way of further illustration, it is desirable to control the level of contact between the device and the tissue in order to form ablation lesions, such as may be formed in treatment of cardiac arrhythmia. In particular, it is desirable to maintain a relatively constant level of contact between the ablation electrode and the cardiac tissue in order to elevate tissue temperature to around 50 degrees C. to form lesions in the cardiac tissue via coagulation necrosis. Such lesions change the electrical properties of the cardiac tissue and may lessen or eliminate undesirable atrial fibrillations when formed at specific locations in cardiac tissue. Insufficient contact during the ablation procedure may result in poor lesion formation.

Tissue contact is not always readily determined using conventional fluoroscopy techniques. Instead, the physician may determine tissue contact based on his/her experience maneuvering the catheter. Such experience only comes with time, and may be lost if the physician does not use the catheter on a regular basis. When used inside the heart, the beating heart further complicates matters by making it difficult to assess and maintain sufficient contact with the tissue for a sufficient length of time. If contact with the tissue cannot be properly maintained, the advantages of using the device may not be fully realized.

BRIEF SUMMARY OF THE INVENTION

It is desirable to be able to assess electrode contact with a moving surface (e.g., a heart wall) for electrophysiology procedures (e.g., tissue ablation). When a flexible conductive polymer electrode is positioned against the heart wall, the beating of the heart deflects the electrode. This deflection may be measured by implementing one or more electro-mechanical sensors in the electrode. The electro-mechanical sensor(s) generate electrical signals in response to movement or flexure of the flexible conductive polymer electrode.

The present invention provides for ablation devices and methods having improved tissue contact properties utilizing flexible conductive polymers.

An objective of the present invention is to provide a flexible conductive polymer electrode that may be used for RF ablation treatment.

Another object of the present invention is to provide a method of manufacturing a contact-sensing electrode assembly for ablation therapy.

Another object of the present invention is to provide a flexible, conductive polymer-based electrode for RF ablation, which can be used in a wide variety of tissue environments.

Yet another object of the invention is to provide an ablation electrode that better concentrates the energy to the region of tissue that is in contact with the electrode.

Yet another object of the invention is to provide an ablation electrode that mitigates edge-effects, hot spots and coagulum formation during the ablation process.

Another object of the present invention is to provide an electrode with a contact sensor assembly that can sense contact with tissue based on the pressure that is exerted on the sensor, and then use the contact information for medical treatments (such as ablation).

Another object of the present invention is to provide an ablation electrode with a contact sensor that measures pressure that is being exerted on the sensor based on mechanical contact between the sensor and another mass, such as tissue.

Yet another object of the present invention is to provide a method of ablation using contact sensing.

Yet another objective of this invention is to provide a method for RF ablation that utilizes a flexible, conductive polymer-based electrode in accordance with the teachings herein.

Disclosed herein is a contact sensing catheter system, including: a catheter shaft having a distal end; a flexible conductive polymer electrode located at the distal end of the catheter shaft; and at least one electro-mechanical contact sensor positioned at least partially within the flexible conductive polymer electrode, wherein the at least one electro-mechanical contact sensor outputs an electrical signal in response to a mechanical force acting thereon. The at least one electro-mechanical contact sensor may be a piezoelectric sensor, such as a laminated piezoelectric film, a strain gauge, or another suitable electro-mechanical contact sensor (e.g., fiber optic sensors). In some embodiments of the invention, the at least one electro-mechanical contact sensor is oriented coaxially to the catheter shaft.

Typically, the electrical signal generated by the at least one electro-mechanical contact sensor is a variable electrical signal that varies in response to variations in the mechanical force acting on the at least one electro-mechanical contact sensor. The system may also include an output device electrically connected to the at least one electro-mechanical contact sensor. The output device receives the electrical signal output by the at least one electro-mechanical contact sensor and presents to a user of the system an indicator of contact between the electrode and a tissue. Thus, the output device may include a contact assessment processor configured to analyze the electrical signal output by the at least one electro-mechanical contact sensor and identify characteristics thereof, such as amplitude and periodicity, indicative of a degree of contact between the flexible conductive polymer electrode and the tissue.

Optionally, the flexible conductive polymer electrode includes a passageway for a coolant fluid to flow therethrough. The passageway may define a loop such that a coolant fluid travels from a proximal end of the electrode, through a distal end of the electrode, and returns to the proximal end of the electrode via the passageway ("closed loop irrigation"). Alternatively, the passageway may include one or more efflux holes to permit the coolant fluid to exit the electrode ("open irrigation").

According to another embodiment of the present invention, a contact sensing catheter system includes: a catheter shaft having an electrode region at a distal end thereof; a flexible conductive polymer electrode mounted to the catheter shaft within the electrode region; at least one electro-mechanical contact sensor positioned at least partially within the electrode region, wherein the at least one electro-mechanical contact sensor outputs an electrical signal in response to a mechanical force acting thereon; and an output device electrically connected to the at least one electro-mechanical contact sensor and configured to present to a user of the system an indicator of contact between the electrode and a tissue, the output device including a contact assessment processor configured to assess a degree of contact between the electrode and the tissue based at least in part on the electrical signal output by the at least one electro-mechanical contact sensor. It is contemplated that the at least one electro-mechanical contact sensor may be housed at least partially within the flexible conductive polymer electrode. It is also contemplated that the at least one electro-mechanical contact sensor may be mounted at least partially on an outer surface of the flexible conductive polymer electrode. By positioning the electro-mechanical contact sensor at least partially within the electrode region, the electro-mechanical contact sensor will be subjected to generally the same stresses as the electrode itself, reducing the occurrence of "false positive" contact readings that might occur if the electro-mechanical sensor is located elsewhere, such as proximal of the electrode within the catheter shaft.

In yet another embodiment, the present invention provides a contact sensing device that includes: a flexible conductive polymer electrode; and at least one electro-mechanical contact sensor positioned at least partially within the flexible conductive polymer electrode.

According to another aspect of the present invention, a method of manufacturing a contact sensing device generally includes the steps of: forming a catheter having a flexible conductive polymer electrode located on a distal end of the catheter; and implanting at least one electro-mechanical contact sensor at least partially within the flexible conductive polymer electrode. The step of implanting at least one electro-mechanical contact sensor at least partially within the flexible conductive polymer electrode may include: providing at least one electro-mechanical contact sensor; and forming the flexible conductive polymer electrode about the at least one electro-mechanical contact sensor. The method may also include electrically coupling the at least one electro-mechanical contact sensor to a monitoring device, whereby the monitoring device receives an electrical signal output by the at least one electro-mechanical contact sensor in response to a mechanical force acting thereon.

Also disclosed herein is a method of sensing contact between a flexible conductive polymer electrode and a tissue. The method generally includes the following steps: providing a flexible conductive polymer electrode having at least one electro-mechanical contact sensor implanted therein; monitoring an electrical signal output by the at least one electro-mechanical contact sensor; and assessing contact between the flexible conductive polymer electrode and the tissue based at least in part on an analysis of the electrical signal output by the at least one electro-mechanical contact sensor.

Typically, the step of assessing contact between the flexible conductive polymer electrode and the tissue will include analyzing the electrical signal output by the at least one electro-mechanical contact sensor for characteristics that are indicative of contact between the flexible conductive polymer electrode and the tissue. For example, a degree of contact between the flexible conductive polymer electrode and the tissue may be assessed based at least in part on an amplitude of the electrical signal output by the at least one electro-mechanical contact sensor. As another example, contact between the flexible conductive polymer electrode and the tissue may be assessed based at least in part on a periodicity of the electrical signal output by the at least one electro-mechanical contact sensor.

An advantage of using a flexible conductive polymer in an ablation device is that the design may be significantly less complicated, which permits reduced manufacturing costs and increased reliability.

Another advantage of using a flexible conductive polymer electrode in an ablation device is improved contact between the electrode and the tissue, which results in a higher efficiency in delivering ablation energy to the tissue.

Still another advantage of the present invention is that it minimizes the occurrence of "false positive" contact readings by subjecting the electro-mechanical contact sensor to substantially the same forces as the flexible conductive polymer electrode.

The foregoing and other aspects, features, details, utilities, and advantages of the present invention will be apparent from reading the following description and claims, and from reviewing the accompanying drawings.

DETAILED DESCRIPTION OF THE INVENTION

A flexible conductive polymer electrode for ablation is disclosed, along with methods for using and methods of manufacturing the flexible conductive polymer electrode. Of course, it is within the spirit and scope of the present invention to use the flexible conductive polymer electrode for other applications, including, but not limited to, electrophysiology studies such as mapping and diagnosis.

As used herein, the term "conductive polymer" refers to a polymer that is formed using at least some conductive materials and which is conductive even in its quiescent state such that the polymer may conduct sufficient energy to ablate tissue. The present invention will work with various conductive polymer materials. For example, U.S. Pat. No. 6,999,821, which is hereby incorporated by reference as though fully set forth herein, discloses intrinsically conductive and conductor-filled polymers that may be useful in the present invention. As disclosed therein, intrinsically conductive polymers include polyacetylene, polypyrrole, and polyanaline, among others. Conductor-filled polymers may include presently available materials approved for implantation such as silicone rubber with embedded metallic, carbon or graphite particles or powder. Silver filled silicone rubbers of the kind manufactured by NuSil or Specialty Silicone Products, modified so as to be approved for implantation, are of potential utility. An example is silver-coated, nickel-filled silicone rubber sold as NuSil R2637.

The substrate need not be silicone; for example, it is contemplated that other insulating or weakly conductive materials (e.g., non-conductive elastomers) may be embedded with conductive materials, conductive alloys, and/or reduced metal oxides (e.g., using one or more of gold, silver, platinum, iridium, titanium, tantalum, zirconium, vanadium, niobium, hafnium, aluminum, silicone, tin, chromium, molybdenum, tungsten, lead, manganese, beryllium, iron, cobalt, nickel, palladium, osmium, rhenium, technetium, rhodium, ruthenium, cadmium, copper, zinc, germanium, arsenic, antimony, bismuth, boron, scandium, and metals of the lanthanide and actinide series, and, if appropriate, at least one electroconductive agent). The conductive material may be in the form of powder, grains, fibers, or other shaped forms. The oxides can be mixtures comprising sintered powders of an oxycompound. The alloy may be conventional, for example titanium boride.

Other examples of conductive polymers that may be used in the present invention include the conductive polymers described and disclosed in U.S. Pat. Nos. 6,646,540, 6,495,069, and 6,291,568, all of which are incorporated by reference as if set forth in their entireties herein.

The conductive polymer may be pressure sensitive, in that the electrical resistance of the electrode may vary inversely in proportion to the pressure that is applied thereto. It should be understood, however, that the flexible conductive polymer electrodes disclosed herein are conductive even in their quiescent state (that is, when not under stress), and are therefore distinguished from the pressure sensitive conductive composite ("PSCC") electrodes disclosed in U.S. application Ser. No. 11/647,316, filed 29 Dec. 2007, which are non-conductive in their quiescent state. Preferably, the conductive polymer material will also meet cytotoxity, hemolysis, systemic toxicity and intracutaneous injection standards.

Figure 1A:
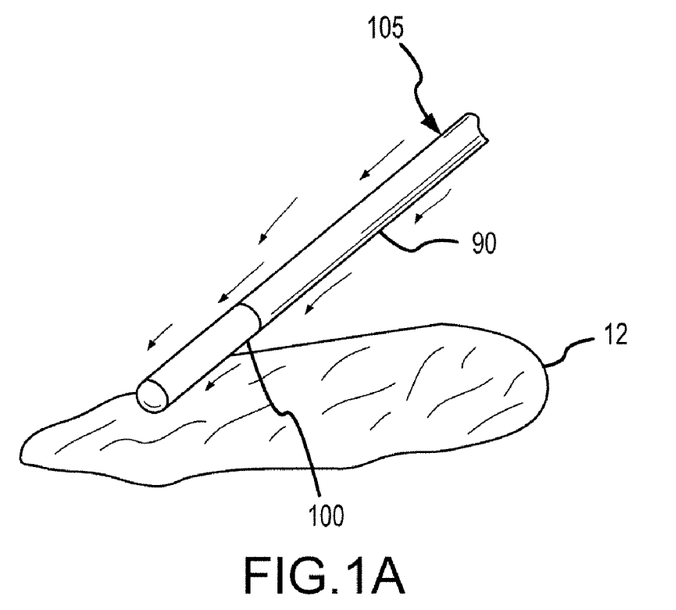
FIGS. 1A and 1B are perspective views of a sample embodiment of the present invention, illustrating how the present invention may be used to ablate tissue.
Figure 1B:
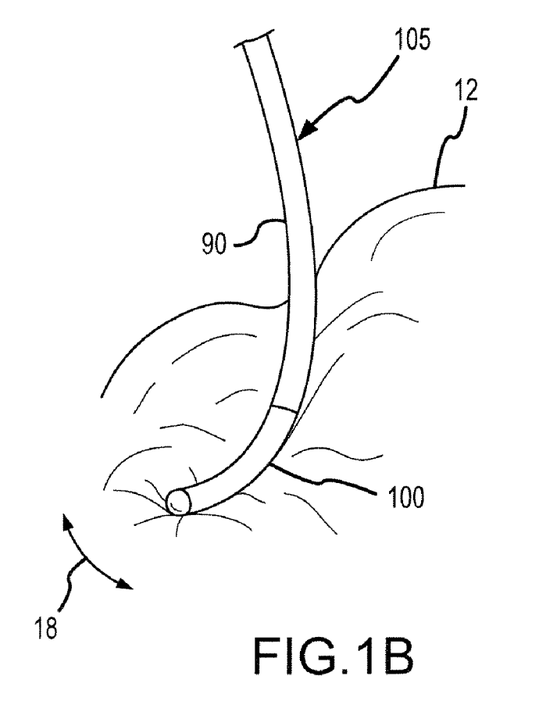

FIGS. 1A and 1B illustrate a sample embodiment of the present invention. As illustrated in FIGS. 1A and 1B, a flexible conductive polymer electrode 105 generally includes a catheter shaft 90 and a contact surface 100 that extends from catheter shaft 90. Electrode 105 is flexible such that when it comes into contact with tissue 12, electrode 105 is deflected in direction 18 as illustrated in FIG. 1B, thereby increasing the contact surface between electrode 105 and tissue 12. Advantageously, this increased contact surface improves the efficacy of, for example, the delivery of ablating energy to the tissue. One of skill in the art will recognize that increasing the force on electrode 105 will tend to increase the contact between electrode 105 and tissue 12, as tissue 12 will tend to "wrap around" electrode 105.

Figure 2:
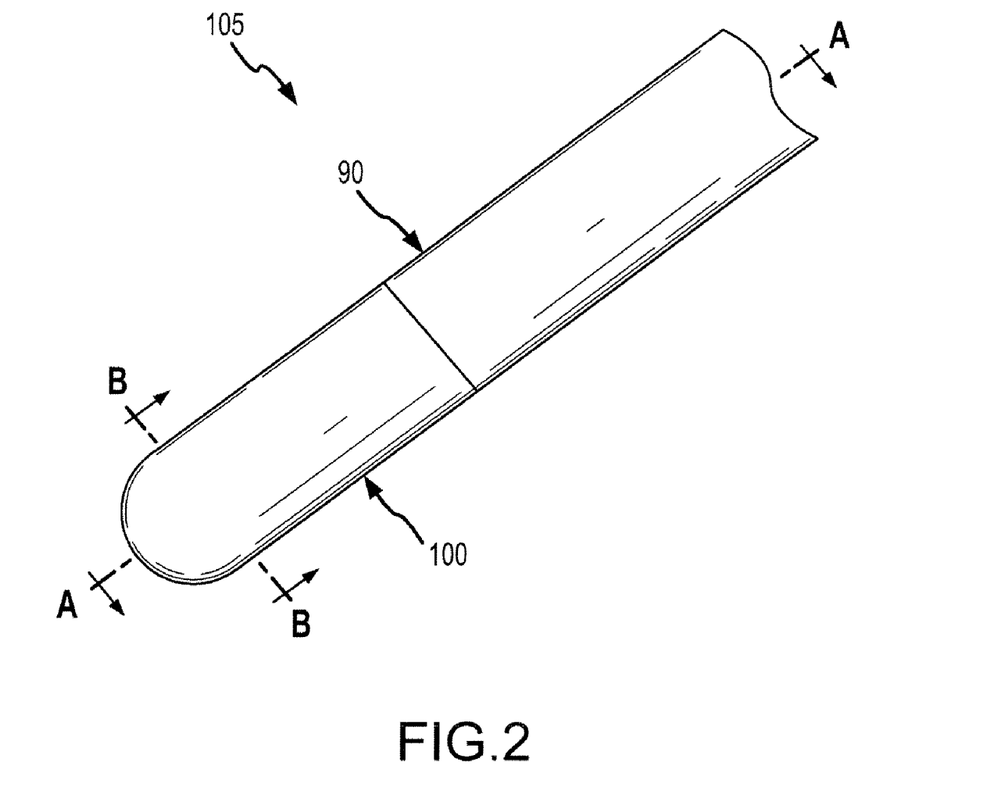
FIG. 2 is a side view drawing of an exemplary catheter having a flexible conductive polymer electrode.

FIG. 2 is a close-up of the sample embodiment depicted in FIGS. 1A and 1B. FIG. 2 illustrates cross-sectional reference lines A-A and B-B, which will be used to illustrate preferred embodiments of the present invention.

Figure 3A:
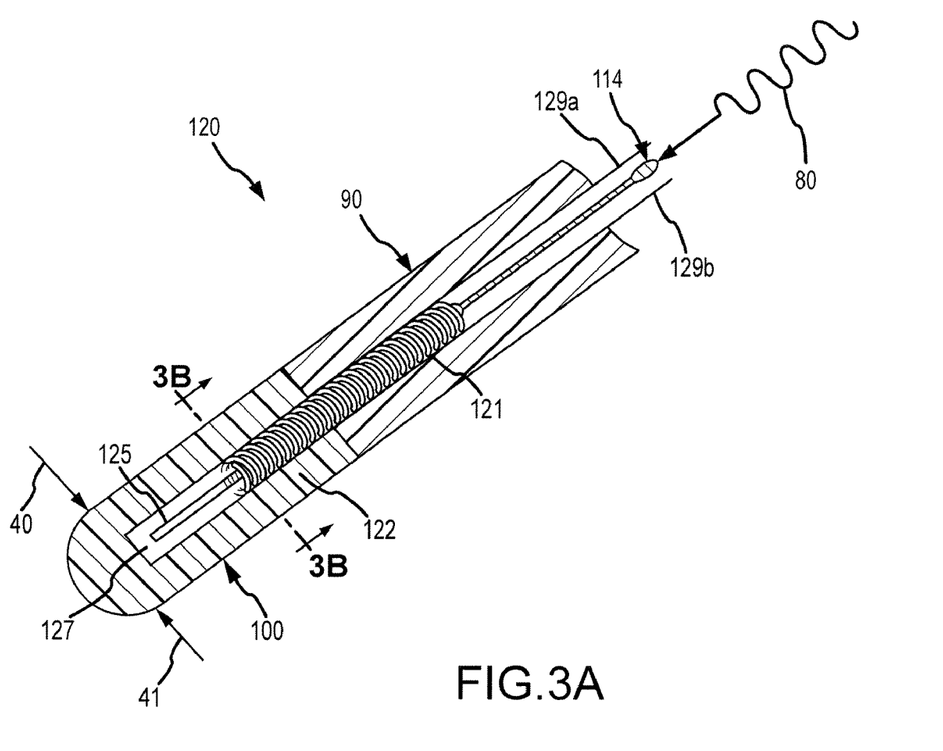
FIGS. 3A and 3B are cross-sectional views of a preferred embodiment in which the conductive element within the flexible conductive polymer electrode is in the shape of a helix.
Figure 3B:
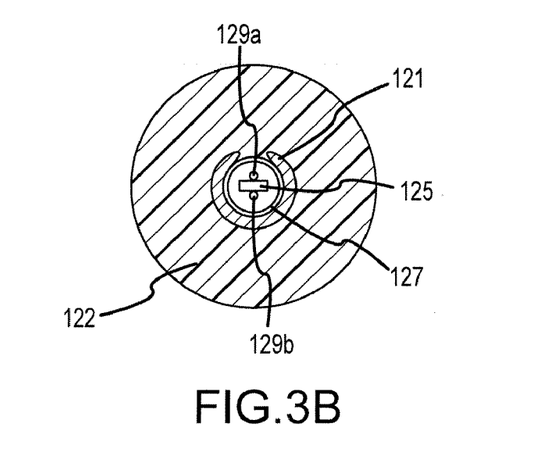

FIGS. 3A and 3B illustrate a preferred embodiment of the present invention, revealing two cross-sectional drawings taken along the lines of A-A and B-B as labeled in FIG. 2. In this preferred embodiment, flexible conductive polymer electrode 120 extends from catheter shaft 90. Catheter shaft 90 may be either conductive or non-conductive, and preferably, catheter shaft 90 is non-conductive. In this embodiment, the flexible conductive polymer forms the working surface 100 of the electrode that is used for ablation therapy.

As depicted in FIGS. 3A and 3B, electrode 120 includes a flexible inner conductive coil 121 in the shape of a helix and a flexible conductive polymer substrate layer 122 within which the inner conductive coil 121 is located. Flexible inner conductive coil 121 may be connected to an electrical conductor 114, which may be connected to an RF generator (e.g., RF current source 80). In use, this preferred embodiment is used to ablate tissue (not shown) to which a reference electrode (not shown) has been attached. Electrode 120 ablates tissue by delivering ablation energy through inner conductive coil 121. Preferably, the reference electrode is grounded to an electrical ground.

Electrode 120 further includes at least one electro-mechanical contact sensor 125 positioned within flexible conductive polymer substrate layer 122. Typically, contact sensor 125 will be positioned within an electrically insulative cavity, such as an electrically insulative tube 127. It is contemplated, however, that contact sensor 125 may simply be coated with an electrically insulative material.

Electrical wiring 129a, 129b may be connected to contact sensor 125 and extend through electrode 120 and catheter shaft 90 to deliver electrical signals from contact sensor 125 to a data acquisition/processing/output device (not shown), such as an echocardioagram (ECG) device. Alternatively, a wireless connection may be implemented, as by providing a transmitter within electrode 120 in association with contact sensor 125 and a receiver in association with the data acquisition/processing/output device.

The term "electro-mechanical contact sensor" is used herein to refer to a sensor that generates an electrical signal in response to application of a mechanical force thereon or thereto. For example, contact sensor 125 may be a piezoelectric sensor, a strain gauge, or any other suitable electro-mechanical contact sensor. For purposes of this disclosure, the invention will be explained in connection with piezoelectric sensors; one of ordinary skill in the art will appreciate how to extend the principles herein for use with other electro-mechanical contact sensors.

Piezoelectric sensors that generate electrical energy in response to applied mechanical stress are well understood in the electro-mechanical arts. In general, piezoelectric sensors include a piezoelectric material containing positive and negative charges. In a neutral or "non-stressed" state, these electrical charges are symmetrically distributed in the piezoelectric material such that the material exhibits an overall neutral electrical charge. However, subjecting the piezoelectric material to a mechanical stress (e.g., flexure, pressure, and/or tension) disturbs the symmetrical distribution of electrical charges, thereby generating electrical energy across the material. Even minor deformation of some piezoelectric materials (e.g., on the order of nanometers) may generate a measurable voltage signal.

Figure 4A:
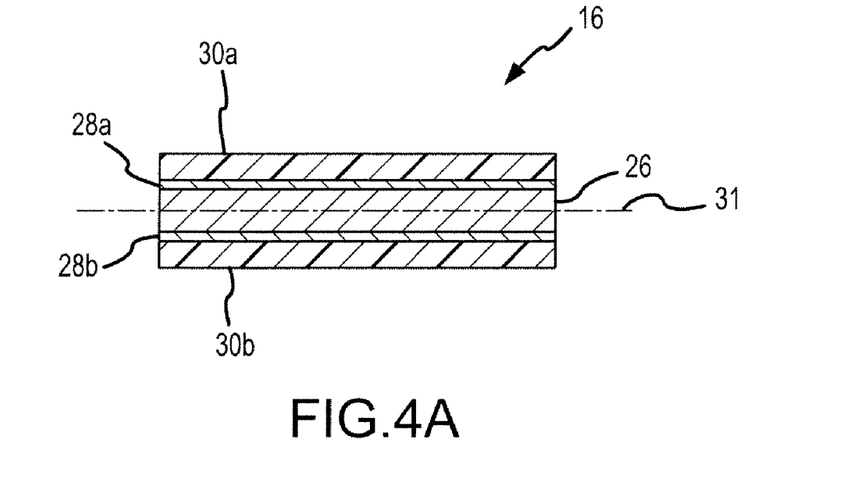
FIG. 4A is a cross-sectional view of an exemplary piezoelectric sensor which may be implemented as an electro-mechanical contact sensor in electrodes according to the present invention.

FIG. 4A is a cross-sectional view of an exemplary piezoelectric sensor 16 which may be implemented for use as contact sensor 125 within the electrode 120. In an exemplary embodiment, the piezoelectric sensor 16 may be a laminated sensor, having a plurality of laminated layers. Laminating the sensor increases its sensitivity.

The laminated layers may include a piezoelectric material 26 "sandwiched" between metal layers 28*a* and 28*b* and protective coating 30*a* and 30*b*. Metal layers 28*a* and 28*b* may be any suitable metal, such as a thin layer of silver ink. The metal layers 28*a* and 28*b* serve to collect electrical charge generated by the piezoelectric material 26, e.g., for delivery as electrical signals via electrical wiring (e.g., 129*a*, 129*b*) to a data acquisition/processing/output device. Metal layers 28*a* and 28*b* serve to collect symmetric electrical energy in response to equiamplitude deflections of the piezoelectric material 26 in either direction, and therefore are particularly desirable for use with bi-directionally deflectable catheters. Protective coating 30*a* and 30*b* may be any suitable material, including, by way of example only, Mylar®.

It is noted that the laminated layers are not limited to any particular material and/or configuration. For example, the piezoelectric sensor 16 is not limited to use with separate metal layers 28*a* and 28*b*. Nor is the piezoelectric sensor 16 limited to the generally rectangular configuration shown in FIG. 4A.

In an exemplary embodiment, the piezoelectric material 26 may comprise a thin, flexible, polymer-based material. One such piezoelectric film is a polyvinylidene fluoride (PVDF) film commercially available from the Sensor Products Division of Measurement Specialties, Inc. (Norristown, Pa.). This PVDF film is approximately 28 μm thick, enabling the PVDF film to be readily housed within the electrode 120 (for example, as shown in FIGS. 3A and 3B).

In addition, this PVDF film has a wide frequency range of about 0.001 Hz to $10^9$ Hz and a high dynamic stress constant ($g_{31}$=216×$10^{-3}$ Vm/N). For purposes of illustration by comparison to other common piezoelectric materials, lead zirconate titanate (PZT) has a dynamic stress constant ($g_{31}$) of 10×$10^{-3}$ Vm/N, while barium titanium oxide ($BaTiO_3$) has a dynamic stress constant ($g_{31}$) of 5×$10^{-3}$ Vm/N. Accordingly, the PVDF film is very sensitive, exhibiting a relatively high voltage response to relatively small mechanical stresses, and is therefore well-suited for measuring dynamic stresses and strains that a moving tissue may exert on the electrode 120.

Of course the piezoelectric sensor 16 described above with reference to FIG. 4A is for purposes of illustration and not intended to be limiting. Other piezoelectric sensors may also be implemented, and are not limited to laminated piezoelectric film. Nor are piezoelectric sensors limited to use with any particular type or size of piezoelectric material. Selection of piezoelectric sensor 16 for use with the electrode 120 may be application-specific and depend at least in part on one or more design considerations, such as, but not limited to, the desired sensitivity and/or spatial constraints for housing the piezoelectric sensor.

Piezoelectric sensor 16 is shown in FIG. 4A in a neutral state. In the neutral state, the piezoelectric material 26 is not subject to any stresses or strains. Accordingly, the electrical charges are symmetrically distributed on either side of the neutral plane 31 in the piezoelectric material 26 such that the material exhibits an overall neutral electrical charge.

Figure 4B:
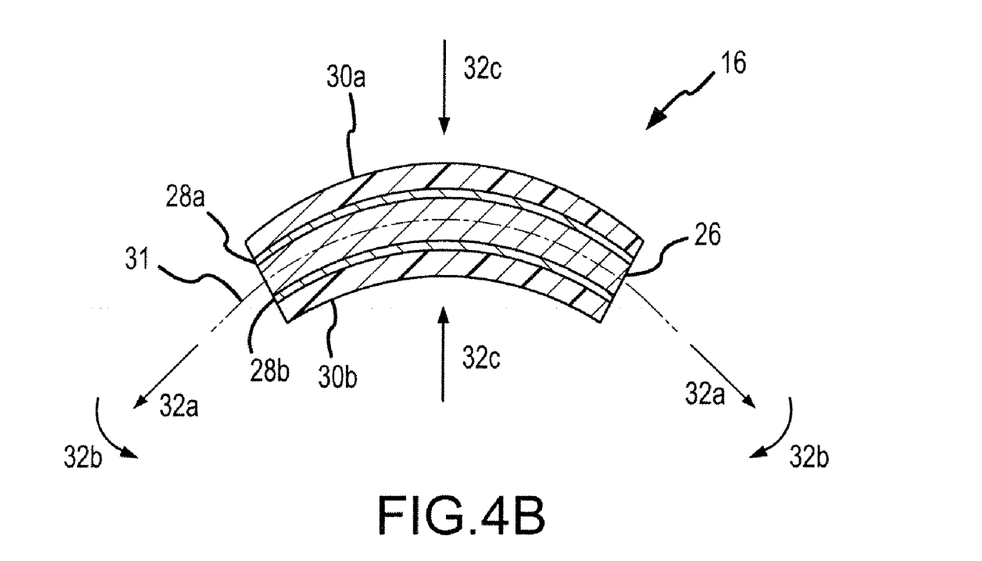
FIG. 4B illustrates the exemplary piezoelectric sensor of FIG. 4A in exaggerated form as it may respond to various stresses.

In FIG. 4B, the piezoelectric sensor 16 is shown in exaggerated form as it may respond to longitudinal stresses applied generally in the direction of arrows 32*a*. In this stressed state, the piezoelectric material 26 longitudinal strain relative to its neutral state. Accordingly, the symmetrical distribution of electrical charges is disturbed, and electrical energy is generated across the piezoelectric material 26. This electrical energy may be collected by metal layers 28*a*, 28*b*, e.g., for delivery as an electrical signal via electrical wiring in the catheter to a data acquisition/processing/output device.

It is noted that the piezoelectric sensor 16 may also respond to bending stresses applied generally in the direction of arrows 32*b*. In this stressed state, the piezoelectric material 26 undergoes flexural strain relative to its neutral state. Accordingly, the symmetrical distribution of electrical charges is disturbed, and electrical energy is generated across the piezoelectric material 26. This electrical energy may be collected by metal layers 28*a*, 28*b*, e.g., for delivery as an electrical signal via electrical wiring in the catheter to a data acquisition/processing/output device.

Furthermore, the piezoelectric sensor 16 may also respond to transverse stresses applied generally in the direction of arrows 32*c*. In this stressed state, the piezoelectric material 26 undergoes transverse strain relative to its neutral state. Accordingly, the symmetrical distribution of electrical charges is disturbed, and electrical energy is generated across the piezoelectric material 26. This electrical energy may be collected by metal layers 28*a*, 28*b*, e.g., for delivery as an electrical signal via electrical wiring in the catheter to a data acquisition/processing/output device.

The contact sensor 125 may be oriented within the electrode 120 to provide the desired sensitivity. By way of example only, contact sensor 125 is shown in FIGS. 3A and 3B as generally centrally oriented within electrode 120, with the plane 31 (see FIG. 4A) of the contact sensor 125 substantially parallel to the central axis/neutral plane of electrode 120. Accordingly, contact sensor 125 is responsive to movement or deflection of electrode 120 relative to its neutral plane (e.g., in the directions of arrows 40 and 41 shown in FIG. 3A).

Other embodiments are also contemplated as being within the scope of the invention. For example, contact sensor 125 is not limited to being centrally oriented in the electrode 120, and may be offset from the central axis/neutral plane of electrode 120. As another example, contact sensor 125 is not limited to being positioned within electrode 120, and may be laminated to an outer surface of the flexible conductive polymer substrate layer 122 (that is, within what may be referred to as an "electrode region" of the catheter shaft 90). One of ordinary skill in the art will also appreciate that multiple electro-mechanical contact sensors may be arranged in any desired configuration (e.g., two electro-mechanical contact sensors arranged substantially orthogonally to each another), with the electro-mechanical contact sensors generally co-located with flexible polymer substrate layer 122 (e.g., housed thereon or mounted thereto). By co-locating the electro-mechanical contact sensors with the flexible polymer substrate layer, the electro-mechanical contact sensors and the flexible polymer substrate layer 122 will experience generally the same mechanical forces. Of course, other configurations are also contemplated as within the spirit and scope of the present invention.

Figure 5:
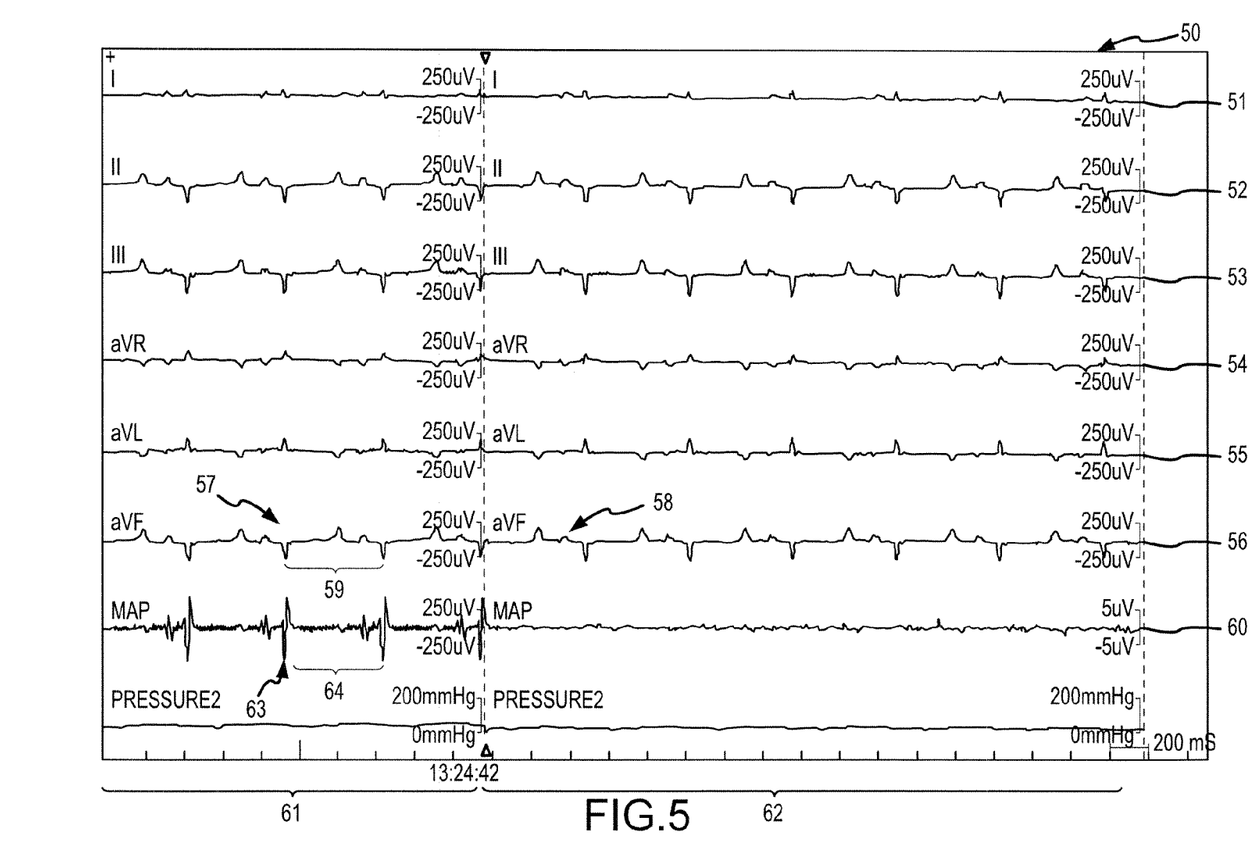
FIG. 5 shows exemplary output of an ECG device showing waveforms corresponding to a patient's heartbeat and a waveform corresponding to electrical signals generated by a piezoelectric sensor in an electrode inserted into the patient's heart.

During operation, contact sensor 125 generates electrical (voltage) signals in response to movement or deflection of electrode 120, and in particular of flexible conductive polymer substrate layer 122, for example as may result from contact between electrode 120 and tissue 12 as shown in FIG. 1A. These electrical signals may be viewed by the user, for example as output on an ECG device. FIG. 5 shows exemplary output 50 of an ECG device showing waveforms 51-56 corresponding to a patient's heartbeat, and a waveform 60 corresponding to electrical signals generated by contact sensor 125 in electrode 120 inserted into the patient's heart.

It is well-understood in the medical sciences that heart wall motion (or heartbeat) is due to electrical signals in the heart that cause myocardial contractions. The heart wall motion may be detected and displayed for a user on an ECG device, e.g., as waveforms 51-56. By way of example, peaks 57 and 58 in waveform 56 correspond to heartbeats. The period (time between heartbeats) is also observed, e.g., as period 59.

Similarly, output from contact sensor 125 may be displayed on the ECG device, e.g., as waveform 60. Accordingly, the output may be implemented to assess dynamic contact between electrode 120 (that is, flexible conductive polymer substrate layer 122) and a moving tissue (e.g., the myocardial wall). In the example shown in FIG. 5, a flexible conductive polymer electrode, such as electrode 120 depicted in FIGS. 3A and 3B, was positioned in good contact with a moving heart wall being monitored (waveforms 51-56) during time 61, and the electrode was removed from contact with the moving heart wall during time 62.

In an exemplary embodiment, the signal strength (e.g., amplitude) from the contact sensor is proportional to the amount of movement or deflection of the electrode, and therefore can be used to determine if the electrode is in good contact with a moving tissue (e.g., the myocardium). For example, the signal strength (as observed by the peaks in waveform 60) is strong during time 61 when the electrode was in good contact with the moving heart wall, and the signal strength is weak when the electrode was removed from contact with the moving heart wall during time 62. Accordingly, the signal strength may indicate a degree of contact between the electrode and moving tissue.

In addition, the output (waveform 60) may be used for dynamic contact assessment. That is, electrical signals are generated by the contact sensor in response to movement of the electrode in which the contact sensor is positioned (or, in some embodiments of the invention, to which the contact sensor is mounted). If the electrode is not in contact with the moving target tissue, or is in contact with a stationary tissue, there are no peaks in the resulting waveform 60 (or the peaks are intermittent). On the other hand, a strong correlation between the heartbeat (e.g., peak 57) and output by the contact sensor (e.g., peak 63) indicates that the electrode is in good contact with the moving target tissue.

Signal periodicity is also a strong indicator of dynamic contact assessment. For example, the period 59 between heartbeats corresponds well with the period 64 between output by the contact sensor, indicating that the electrode is moving in response to the heartbeat (and not some other reason).

It is observed in FIG. 5 that output from the contact sensor (waveform 60) corresponds with both the peaks and the periodicity of the patient's heartbeat (waveforms 51-56). Therefore, the user is able to use this output for assessing the degree of contact between the electrode and the moving heart wall, e.g., for an ablation procedure. The user may also assess the degree of contact between the electrode and the moving heart wall. In an exemplary embodiment, higher amplitude output (e.g., in waveform 60) indicates more contact, and lower amplitude indicates less contact. The user can use this feedback to increase or decrease contact of the electrode with the moving heart wall to achieve the desired contact.

Before continuing, it is noted that although the waveforms shown in FIG. 5 are output on an ECG device such as may be used for monitoring a patient's heartbeat, the present invention is not limited to use with any particular type of output device. Any suitable analog and/or digital device may be implemented for indicating electrode-tissue contact to a user. In another exemplary embodiment, the electrical signals generated by the contact sensor may be further characterized using a suitable processing device such as, but not limited to, a desktop or laptop computer. Such processing device may be implemented to receive the voltage signal generated by the contact sensor and convert it to a corresponding contact condition for the flexible conductive polymer electrode and output for the user, e.g., at a display device.

Of course the output device is not limited to a display device. For example, the electrode-tissue contact may be output to the user as an audio signal or tactile feedback (e.g., vibrations) on the handle of the catheter to which the electrode is mounted or attached. In any event, circuitry for conveying output of the contact sensor to a user in one form or another may be readily provided by those having ordinary skill in the electronics arts after becoming familiar with the teachings herein.

One of ordinary skill in the art will also appreciate that, because the flexible conductive polymer electrode is conductive in its quiescent state, it may also be used to measure electrical coupling between the electrode and tissue using phase angle. By dynamically sensing physical contact (e.g., using electro-mechanical contact sensors) in conjunction with sensing electrical coupling through phase angle, efficacy of treatment can be advantageously enhanced.

Figure 6A:
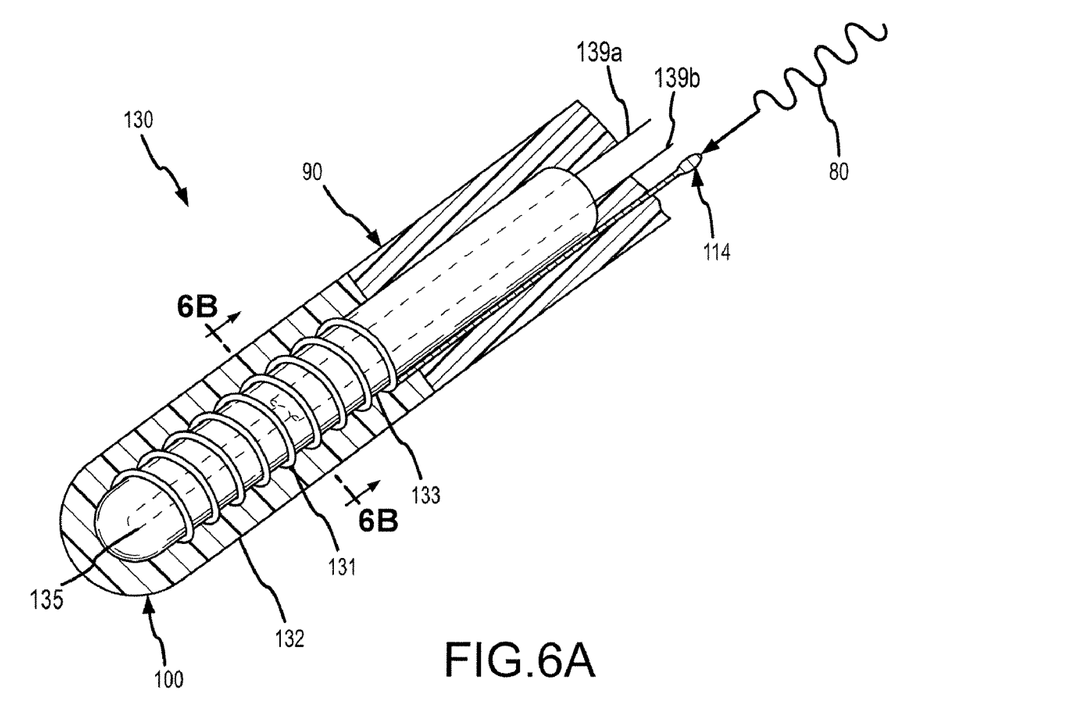
FIGS. 6A and 6B are cross-sectional views of another preferred embodiment in which the electrode is located about a flexible inner core.
Figure 6B:
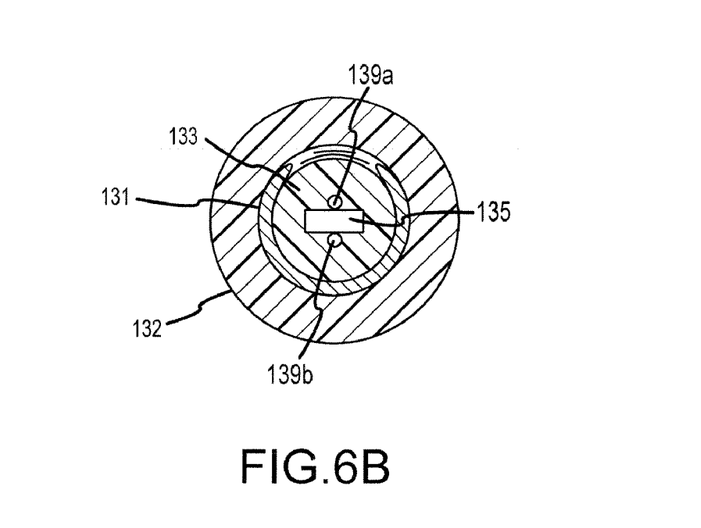

FIGS. 6A and 6B illustrate yet another preferred embodiment of the present invention, revealing two cross sectional drawings taken along the reference lines of A-A and B-B as labeled in FIG. 2. Electrode 130 extends from a catheter shaft 90 and generally includes: flexible inner conductive coil 131 in the shape of a helix; an outer flexible conductive polymer substrate layer 132; and a flexible shaft 133 located within the helix of the flexible inner conductive coil 131.

Flexible shaft 133 is preferably an electrically insulative shaft, but may be electrically conductive without departing from the spirit and scope of the present invention. Moreover, flexible shaft 133 is preferably thermally conductive, as described in further detail below. Flexible shaft 133 may optionally include a portion of a sphere on its distal end as shown in FIG. 6A.

Contact sensor 135 is positioned within flexible shaft 133 (as shown in phantom in FIG. 6A). Also illustrated in FIGS. 6A and 6B are electrical conductors 139a, 139b to deliver the electrical signal output by contact sensor 135 to a data acquisition/processing/output device (not shown), such as an ECG.

Flexible inner conductive coil 131 is connected to an electrical conductor 114, which may be connected to an RF generator (e.g., RF current source 80). In use, this preferred embodiment is used to ablate tissue (not shown) to which a reference electrode (not shown) has been attached. Electrode 130 ablates tissue by delivering energy through inner conductive coil 131. Preferably, the reference electrode is grounded to an electrical ground reference signal.

As one of ordinary skill can appreciate, temperature sensors (such as thermistors, thermocouples or other temperature sensors) can be used to monitor operation temperature to help ensure effective and safe ablation treatment. For example, one or more temperatures may be used at a variety of locations, including, for example, at a distal end of the device to monitor a temperature that is at least in part reflective of the tissue temperature, or even within the electrically insulative shaft. Other potential locations include the use of a temperature sensor located at a location where a cooling fluid enters or exits the device. Of course, temperature sensors may be located at additional or different locations. A heat sink may also be employed to help prevent the electrode from overheating the electrode and the tissue.

Electrical conductor 114 may be implemented using a single conductive wire or multiple strands of wire. Preferably, the wires are made of flexible conductive materials which allow the surface contacting area of the electrode to be bent and formed into various shapes to provide better contact with the tissue (e.g., an increased contact area between the electrode and the tissue). Acceptable materials include, but are not limited to, stainless steel, nickel titanium (e.g., Nitinol), tantalum, copper, platinum, iridium, gold, or silver, and combinations thereof. Preferably, the material used to manufacture the conductive element is a bio-compatible electrically conductive material, such as platinum, gold, silver, nickel titanium, and combinations thereof. Other electrically conductive materials coated with bio-compatible materials may also be employed, including for example, gold-plated copper. Finally, it is also contemplated that electrically conductive polymers may also be used provided they are bio-compatible or coated with a bio-compatible material.

The present invention permits the construction of a flexible conductive polymer RF ablation electrode that can be used in a wide variety of different tissue environments, including for example, tissues having varying degrees of elasticity and contour.

While the embodiments disclosed in the attached figures disclose an electrode that is generally cylindrical in shape, the present invention also contemplates that the electrode may be formed into various shapes to better fit the contour of the target tissue. In one embodiment, for example, the electrode can be made long enough to strap around and form a noose around the pulmonary veins in epicardial applications. Particularly, electrical conductor 114 that is coupled to the RF energy source may be formed into a desired shape and then the flexible conductive polymer layer may be formed over the conductive element and electro-mechanical contact sensor in the preferred shape. For example, the electrode may be shaped like a spatula for certain applications, including for example, minimally invasive sub-xyphoid epicardial applications, where the spatula shape will permit easy placement and navigation in the pericardial sac. Because the conductive polymers used herein are flexible materials, they can be used to form electrodes having a great variety of shapes, including a spatula.

Alternatively, the electrically conductive element that is coupled to the RF energy source (e.g., 121, 131) may be formed using shape-memory retaining material, such as Nitinol, which would permit the electrode to be fitted to specific preset geometries, such as the ostium of a pulmonary vein, such that the electrode is shaped to provide a desired contact pressure pattern on the tissue due to the deformation of the wire when pressed against the tissue.

Similarly, while the reference to insulative shaft (for example, 133) is generally used in connection with a generally cylindrical member, it is contemplated by the present invention that the insulative shaft could be in a geometric shape other than a cylinder, including, for example, a noose, a spatula, or the shape of the ostium of a pulmonary vein. For purposes of this application, the term "insulative shaft" is intended to encompass shapes in addition to a cylindrical shaft.

Whenever it is desired that the conductive element that is coupled to the RF energy source be formed in the shape of a helix, such as is the case with elements 121 and 131, the coil may be chosen to be of a specific stiffness (that is, having a characteristic spring constant) that would allow the coil to exert a desired amount of pressure when the electrode bends or deflects upon contact with the tissue. One of skill in the art would understand that the degree of desired contact pressure would depend in part upon the elastic property of the tissue being contacted with the electrode. For example, the atrial wall may require less contact pressure than the ventricular wall. Thus, electrodes of varying stiffness can be designed for application in different tissues and different regions of the heart.

In some embodiments, for example, as depicted in FIGS. 6A and 6B, the conductive element may be mounted on an insulative shaft. The conductive element can be shaped in any number of ways, including for example, a coil, mesh, coating or wrap. The insulative shaft provides additional mechanical support in applications that require greater amounts of axial force and torque. The insulative shaft may be made of any electrically insulative material, including, for example, polyurethane. Preferably, the insulative shaft is made of a biocompatible, electrically insulative material.

Generally, flexibility is a very desirable characteristic in a catheter. Some applications, however, may require relatively more or less flexibility. Thus, it is contemplated that the same structural design may be used to produce ablation devices of varying flexibility, for example by varying the materials employed in constructing the ablation device.

In other embodiments, the conductive element is mounted on an electrically insulative, thermally conductive shaft. The thermally conductive shaft may improve the cooling of the electrode and the electrode-tissue interface temperature during ablation by thermally conducting the heat from the interface to the ambient flowing blood in endocardial applications. In addition, the thermally conductive shaft can be instrumented with thermal sensors that can be used for temperature controlled RF ablation. The thermally conductive shaft may be made of any electrically insulative, thermally conductive material, including, for example, CoolPoly® thermally conductive, electrically insulative plastic. Preferably, the thermally conductive shaft is made of a biocompatible, thermally conductive, electrically insulative material.

In still other embodiments, the cooling efficiency of the ablation electrode can be enhanced by mounting a heat sink at the proximal end of the electrode (that is, near the interface between the electrode and the catheter shaft). The heat sink will typically include a material with high thermal conductivity. The use of a heat sink may be particularly useful for small electrodes (typically around 10 mm or less), or for sectioned electrodes that may give rise to hot spots. The heat sink may be made of any electrically insulative, thermally conductive material, including, for example, thermally conductive polyurethane (e.g., polyurethane with thermally conductive ceramic powder embedded therein), diamond, aluminum nitride, boron nitride, silicone, thermal epoxy and thermally conductive, electrically insulative plastics.

In yet another embodiment, the electrically insulative member may contain one or more passageways for carrying cooling fluids (e.g., saline solution) to the distal end of the electrode. Alternatively, one or more of the passageways may be further defined by a cooling tube made of the same material as, or a material different from, the insulative member. Of course, it is contemplated that the cooling tube and the electrically insulative member may be one in the same (that is, the electrically insulative member itself may define the fluid passageway). If a cooling tube is used in addition to the passageway, the portion of the cooling tube that is located within the catheter shaft is preferably thermally and electrically insulative, while the portion of the cooling tube that is located within the electrode is preferably thermally conductive. The thermally insulative tube inside the catheter shaft is to minimize the degree to which the cooling fluid is heated to body temperature as the result of thermal conduction through the catheter shaft wall as the fluid travels from the outside fluid source through the catheter shaft and to the electrode. The thermally conductive tube inside the electrode, on the other hand, is intended to cool the electrode and the electrode-tissue interface during ablation by thermally conducting the heat from the interface to the flowing fluid inside the tube.

In yet another embodiment, the electrically insulative member may contain one or more passageways for carrying cooling fluids to the actual electrode-tissue interface. The passageways include an inlet to the electrode, and at least one outlet, such as a fluid efflux hole at the distal end of the electrode. Moreover, one or more thermal sensors may be placed in or near the fluid passageway, for example, to measure the temperature of the coolant at the inlet and/or at the outlet. The temperature difference between the inlet and outlet during ablation could be used to monitor the efficacy of the electrode-tissue interface cooling and also to perform temperature-controlled ablation. One or more of the passageways may alternatively be further defined by a cooling tube, which may be made of the same material as, or a material different from, the insulative member, and which, in some embodiments, may be at least partially defined by the insulative member. If a cooling tube is used in addition to the passageway, the portion of the cooling tube that is located within the catheter shaft is preferably thermally insulative, while the portion of the cooling tube that is located within the electrode is preferably thermally and electrically conductive. The thermally insulative tube inside the catheter shaft is to minimize the degree to which the cooling fluid is heated to body temperature as the result of thermal conduction through the catheter shaft wall as the fluid travels from the outside fluid source through the catheter shaft and to the electrode. The thermally conductive tube inside the electrode, on the other hand, is intended to cool the electrode and the electrode-tissue interface during ablation by thermally conducting the heat from the interface to the flowing fluid inside the tube.

Figure 7A:
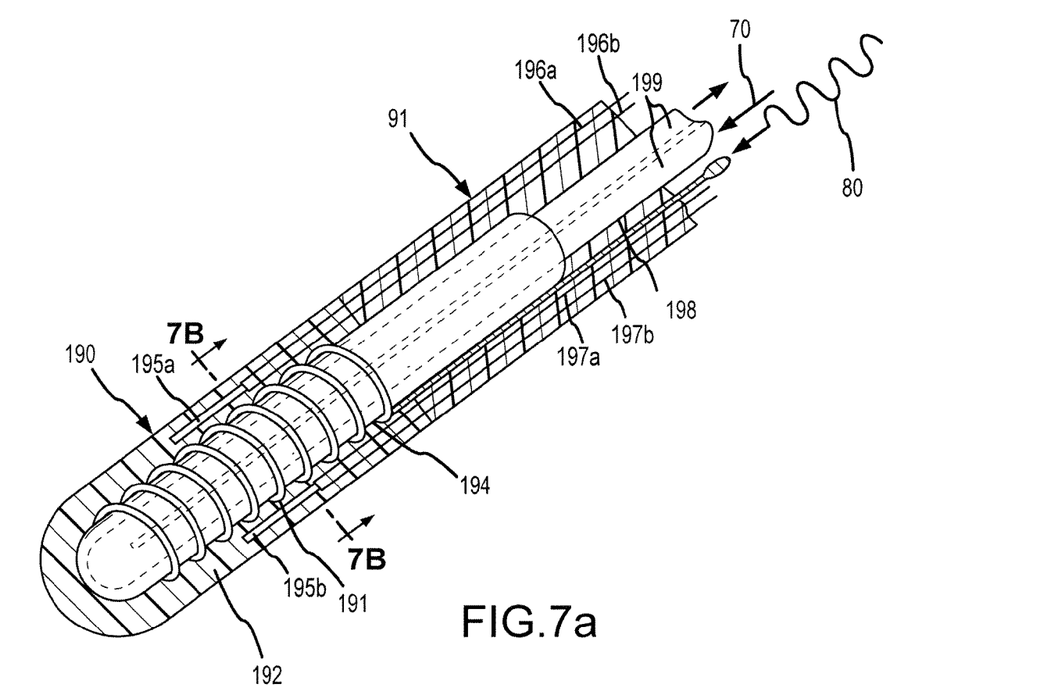
FIGS. 7A and 7B are cross-sectional views of still another preferred embodiment including a closed-loop fluid cooling system.
Figure 7B:
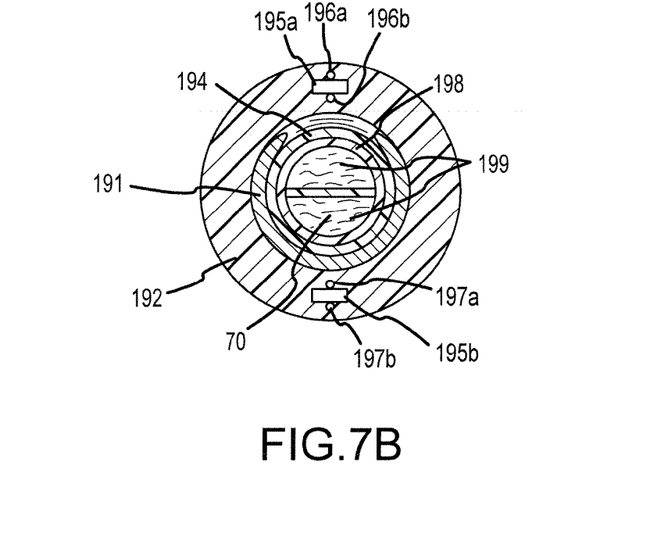

FIGS. 7A and 7B, which reveal two cross-sectional drawings taken along the reference lines A-A and B-B as labeled in FIG. 2, illustrate a closed-loop irrigated catheter according to an embodiment of the present invention. Electrode 190 extends from a catheter shaft 91 and is connected to an RF energy source (e.g., RF current source 80). Electrode 190 generally includes: flexible inner conductive coil 191 in the shape of a helix; an outer flexible conductive polymer substrate layer 192; a thermally conductive flexible shaft 198 located partially within the helix of the flexible inner conductive coil 191; and closed loop cooling passageway 199 located within the flexible shaft 198. Dual contact sensors 195a, 195b, and their associated electrical wiring 196a, 196b, and 197a, 197b, respectively, are also visible in FIGS. 7A and 7B.

Note that a thermally conductive, electrically insulative sleeve 194 may optionally be located between the flexible shaft 198 and inner conductive coil 191. It is contemplated that sleeve 194 may be eliminated, in which case the inner conductive coil 191 may be thermally coupled directly to flexible shaft 198 and closed loop cooling passageway 199. In this embodiment, thermally conductive flexible shaft 198 and closed loop cooling passageway 199 form a closed loop cooling system in which a cooling fluid 70 (e.g., saline) may flow through passage way 199 to cool the distal tip of the catheter during ablation. In other embodiments of the invention, the fluid passageway includes one or more fluid efflux holes to permit the coolant to exit the electrode (e.g., a fluid efflux hole at the tip of the electrode 190).

It is contemplated that one or more fluid efflux holes may be provided to permit the coolant to exit the electrode. For example, the electrode may include a single coolant efflux hole at its distal end. Alternatively, multiple fluid efflux holes may be arranged along the electrode, for example along its length and/or around its circumference. It may also be desirable to include one or more fluid efflux holes at the junction between the electrode and the catheter shaft.

An irrigated electrode as described above advantageously enhances cooling of both the electrode and the tissue being treated. The coolant flowing through the fluid passageways and out the efflux holes cools the electrode first, and then cools the adjacent tissue by thermal conduction. The flexibility of the irrigated electrode permits the electrode to more closely conform to the tissue surface. This conformance increases the contact area between the electrode and the tissue being treated, which in turn enhances conductive heat transfer from and cooling of the tissue.

By co-locating the flexible conductive polymer electrode and the electro-mechanical contact sensor (e.g., by housing the electro-mechanical contact sensor within the flexible conductive polymer layer or by mounting the electro-mechanical contact sensor on the flexible conductive polymer layer), the present invention advantageously reduces the likelihood of "false positive" contact detections. In particular, the present invention subjects the electro-mechanical contact sensor to substantially the same mechanical forces as the electrode, such that there is a desirably close and generally predictable relationship between the mechanical forces acting on the electrode and the electrical signal output by the electro-mechanical contact sensor.

In an optional embodiment, any of the electrode designs above may be combined with a processor that monitors the RF current that is being delivered by the RF power source 80. In a preferred embodiment, a computer processor (not shown) will monitor the maximum current being delivered and use this information to help control the ablation process. Using this information, the computer processor (not shown) may decrease or increase the power level of the RF power source. By way of example only, the computer processor (not shown) may be used to limit the total amount of RF energy that is delivered to a certain tissue area. Depending on the nature of the tissue, the power level may be increased to improve lesion creation.

The RF source to be used with the present invention is preferably within the radio frequency range of 200-800 kHz, and more preferably with 250 kHz-550 kHz. The source is preferably capable of delivering up to 150 Watts of electrical power.

The embodiments above may be manufactured in a variety of ways. One such method involves forming an electrode assembly as follows. An electrically insulative shaft may be formed using known electrically insulative materials (which may be thermally conductive or thermally insulative). The shaft is preferably formed of flexible materials. At least one electro-mechanical contact sensor may be provided within or on the electrically insulative shaft. An electrically conductive element for conducting RF energy may be formed on at least a portion of the electrically insulative shaft. In accordance with the teachings above, the conductive element is preferably flexible. A layer of flexible conductive polymer may be formed over at least a portion of the conductive element. In accordance with the teachings above, the electrode assembly may be optionally coated with one or more conductive layers, which are preferably flexible. Preferably, the optional layers are made of a biocompatible, electrically conductive material.

An alternative way to manufacture an electrode assembly of the present invention is as follows. An electrically conductive flexible shaft may be formed using known electrically insulative materials. A layer of flexible conductive polymer may be formed over at least a portion of the conductive shaft and at least one electro-mechanical contact sensor. In accordance with the teachings above, the electrode assembly may be optionally coated with one or more flexible conductive layers. Preferably, the optional layers are made of a biocompatible, electrically conductive material.

The electrode assemblies above may also be formed with a fluid lumen and/or one or more fluid efflux holes to permit a cooling fluid to be delivered through the electrode and/or to the tissue during ablation. The assemblies may also be manufactured to include one or more thermal sensors using techniques that are applicable to other known catheter devices. This is described in further detail in U.S. application Ser. No. 11/963,430, filed concurrently herewith and expressly incorporated by reference as though fully set forth herein.

It is contemplated that each of the embodiments discussed above may optionally be used in connection with one or more electrically-conductive outer coverings. Preferably, the outer covering is electrically conductive, such as a flexible wire mesh, a conductive fabric, a conductive polymer layer (which can be porous or nonporous), or a metal coating. The outer covering may be used to not only increase the mechanical integrity, but to enhance the device's ability to assess the tissue contact (for example, when measuring electrical characteristics using a reference electrode connected to the target tissue or when using the flexible conductive polymer electrode to measure phase angles). In some cases, the outer covering may be made using a biocompatible material in order to help make the overall assembly biocompatible. Preferably the outer covering is flexible.

Although multiple embodiments of this invention have been described above with a certain degree of particularity, those skilled in the art could make numerous alterations to the disclosed embodiments without departing from the spirit or scope of this invention. For example, although the present invention has been described in connection with piezoelectric sensors and strain gauges, other electro-mechanical contact sensors may also be employed to good advantage according to the teachings of the present invention. One of skill in the art will also appreciate that the various principles and features described above may be employed in numerous combinations and permutations in accordance with the spirit and scope of the present invention.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A contact sensing catheter system, comprising:
a catheter shaft having a distal end;
a flexible pressure sensitive conductive polymer electrode located at the distal end of the catheter shaft; and
at least one electro-mechanical contact sensor positioned at least partially within the flexible pressure sensitive conductive polymer electrode, wherein the at least one electro-mechanical contact sensor outputs an electrical signal in response to a mechanical force acting thereon.

2. The system according to claim 1, wherein the at least one electro-mechanical contact sensor comprises a piezoelectric sensor.

3. The system according to claim 2, wherein the piezoelectric sensor comprises a laminated piezoelectric film.

4. The system according to claim 1, wherein the at least one electro-mechanical contact sensor comprises a strain gauge.

5. The system according to claim 1, wherein the flexible pressure sensitive conductive polymer electrode further comprises a passageway for a coolant fluid to flow therethrough.

6. The system according to claim 5, wherein the passageway defines a loop such that a coolant fluid travels from a proximal end of the flexible pressure sensitive conductive polymer electrode, through a distal end of the flexible pressure sensitive conductive polymer electrode, and returns to the proximal end of the flexible pressure sensitive conductive polymer electrode via the passageway.

7. The system according to claim 1, further comprising an output device electrically connected to the at least one electro-mechanical contact sensor, the output device receiving the electrical signal output by the at least one electro-mechanical contact sensor and presenting an indicator of contact between the flexible pressure sensitive conductive polymer electrode and a tissue.

8. The system according to claim 1, wherein the electrical signal generated by the at least one electro-mechanical contact sensor is a variable electrical signal that varies in response to variations in the mechanical force acting on the at least one electro-mechanical contact sensor.

9. The system according to claim 8, further comprising a contact assessment processor that assesses a degree of contact between the flexible pressure sensitive conductive polymer electrode and a tissue based at least in part on an amplitude of the variable electrical signal.

10. The system according to claim 8, further comprising a contact assessment processor that assesses contact between the flexible pressure sensitive conductive polymer electrode and a tissue based at least in part on a periodicity of the variable electrical signal.

11. The system according to claim 1, wherein the at least one electro-mechanical contact sensor is oriented coaxially to the catheter shaft.

12. A contact sensing catheter system, comprising:
a catheter shaft having an electrode region at a distal end thereof;
a flexible pressure sensitive conductive polymer electrode mounted to the catheter shaft within the electrode region;
at least one electro-mechanical contact sensor positioned at least partially within the electrode region, wherein the at least one electro-mechanical contact sensor outputs an electrical signal in response to a mechanical force acting thereon; and
an output device electrically connected to the at least one electro-mechanical contact sensor and configured to present to a user of the system an indicator of contact between the flexible pressure sensitive conductive polymer electrode and a tissue, the output device including a contact assessment processor configured to assess a degree of contact between the flexible pressure sensitive conductive polymer electrode and the tissue based at least in part on the electrical signal output by the at least one electro-mechanical contact sensor.

13. The system according to claim 12, wherein the at least one electro-mechanical contact sensor is housed at least partially within the flexible pressure sensitive conductive polymer electrode.

14. The system according to claim 12, wherein the at least one electro-mechanical contact sensor is mounted at least partially on an outer surface of the flexible pressure sensitive conductive polymer electrode.

15. The system according to claim 12, wherein the at least one electro-mechanical contact sensor is selected from the group consisting of piezoelectric sensors, strain gauges, fiber-optic sensors, and any combinations thereof.

16. A contact sensing device, comprising:
   a flexible pressure sensitive conductive polymer electrode; and
   at least one electro-mechanical contact sensor positioned at least partially within the flexible pressure sensitive conductive polymer electrode.

17. A method of manufacturing a contact sensing device, the method comprising:
   forming a catheter having a flexible pressure sensitive conductive polymer electrode located on a distal end of the catheter; and
   implanting at least one electro-mechanical contact sensor at least partially within the flexible pressure sensitive conductive polymer electrode.

18. The method according to claim 17, further comprising electrically coupling the at least one electro-mechanical contact sensor to a monitoring device, whereby the monitoring device receives an electrical signal output by the at least one electro-mechanical contact sensor in response to a mechanical force acting thereon.

19. The method according to claim 17, wherein the step of implanting at least one electro-mechanical contact sensor at least partially within the flexible pressure sensitive conductive polymer electrode comprises:
   providing at least one electro-mechanical contact sensor; and
   forming the flexible pressure sensitive conductive polymer electrode about the at least one electro-mechanical contact sensor.

20. A method of sensing contact between a flexible conductive polymer electrode and a tissue, the method comprising:
   providing a flexible pressure sensitive conductive polymer electrode having at least one electro-mechanical contact sensor implanted therein;
   monitoring an electrical signal output by the at least one electro-mechanical contact sensor; and
   assessing contact between the flexible pressure sensitive conductive polymer electrode and the tissue based at least in part on an analysis of the electrical signal output by the at least one electro-mechanical contact sensor.

21. The method according to claim 20, wherein the step of assessing contact between the flexible pressure sensitive conductive polymer electrode and the tissue comprises analyzing the electrical signal output by the at least one electro-mechanical contact sensor for characteristics that are indicative of contact between the flexible pressure sensitive conductive polymer electrode and the tissue.

22. The method according to claim 21, wherein the step of analyzing the electrical signal output by the at least one electro-mechanical contact sensor for characteristics that are indicative of contact between the flexible pressure sensitive conductive polymer electrode and the tissue comprises assessing a degree of contact between the flexible pressure sensitive conductive polymer electrode and the tissue based at least in part on an amplitude of the electrical signal output by the at least one electro-mechanical contact sensor.

23. The method according to claim 21, wherein the step of analyzing the electrical signal output by the at least one electro-mechanical contact sensor for characteristics that are indicative of contact between the flexible pressure sensitive conductive polymer electrode and the tissue comprises assessing contact between the flexible pressure sensitive conductive polymer electrode and the tissue based at least in part on a periodicity of the electrical signal output by the at least one electro-mechanical contact sensor.

\* \* \* \* \*